United States Patent
Dunn et al.

[11] Patent Number: 5,975,096
[45] Date of Patent: *Nov. 2, 1999

[54] LIQUID WASTE DISPOSAL AND CANISTER FLUSHING SYSTEM AND METHOD

[75] Inventors: James L. Dunn; Timothy A. Carty, both of Topeka, Kans.

[73] Assignee: Dornoch Medical Systems, Inc., Riverside, Mo.

[*] Notice: This patent is subject to a terminal disclaimer.

[21] Appl. No.: 08/848,576

[22] Filed: Apr. 28, 1997

Related U.S. Application Data

[63] Continuation-in-part of application No. 08/698,940, Aug. 16, 1996, Pat. No. 5,776,260.

[51] Int. Cl.⁶ ........................................................ B08B 9/08
[52] U.S. Cl. ................................. 134/56 R; 134/104.1; 134/167 R; 134/168 R; 134/169 R; 134/186; 134/116; 134/177
[58] Field of Search ................................ 134/22.18, 22.1, 134/24, 26, 18, 56 R, 57 R, 58 R, 116, 177, 135, 104.1, 104.2, 113, 150, 167 R, 168 R, 169 R, 186

[56] References Cited

U.S. PATENT DOCUMENTS

| | | |
|---|---|---|
| 1,693,885 | 12/1928 | Butterworth . |
| 1,827,085 | 10/1931 | Huff . |
| 2,370,775 | 3/1945 | Capita ........................................ 134/24 |
| 2,641,270 | 6/1953 | Allen . |
| 2,896,643 | 7/1959 | Ottoson ................................... 134/113 |
| 3,078,861 | 2/1963 | Miller ...................................... 134/170 |
| 3,122,151 | 2/1964 | Chambers ............................... 134/170 |
| 3,603,328 | 9/1971 | Fenn . |
| 3,780,757 | 12/1973 | Jordan . |
| 3,791,394 | 9/1973 | Hammelmann . |
| 3,897,599 | 8/1975 | Artzer . |
| 3,989,046 | 11/1976 | Pannier, Jr. et al. . |
| 4,058,412 | 11/1977 | Knapp . |
| 4,306,557 | 12/1981 | North . |
| 4,430,084 | 2/1984 | Deaton . |
| 4,455,140 | 6/1984 | Jostin . |
| 4,675,011 | 6/1987 | Kurtz et al. . |
| 4,809,860 | 3/1989 | Allen . |
| 4,863,446 | 9/1989 | Parker . |
| 4,905,325 | 3/1990 | Colditz . |
| 4,957,491 | 9/1990 | Parker . |
| 4,961,440 | 10/1990 | Wright . |
| 5,011,470 | 4/1991 | Kurtz et al. . |
| 5,024,613 | 6/1991 | Vasconcellos et al. . |
| 5,186,195 | 2/1993 | Wall . |
| 5,217,038 | 6/1993 | Pinder . |
| 5,460,193 | 10/1995 | Levallois et al. . |
| 5,620,428 | 4/1997 | Hand . |
| 5,683,371 | 11/1997 | Hand . |
| 5,688,255 | 11/1997 | Hang . |
| 5,807,359 | 9/1998 | Bemis et al. . |

FOREIGN PATENT DOCUMENTS 650678  8/1979  U.S.S.R. .

*Primary Examiner*—Frankie L. Stinson
*Attorney, Agent, or Firm*—Rudnick & Wolfe

[57] ABSTRACT

A liquid waste disposal and canister flushing system includes a cabinet with a sink for receiving the canister and a subsink for receiving a lower portion thereof. The subsink is connected to a drain line. A plunger subassembly includes a stopper which functions as a drain valve for the canister. An injection jet is connected to water and cleaning solution sources and discharges diluted cleaning solution into the canister for flushing same. The injection jet engages the plunger subassembly for ejecting the stopper from a canister drain opening. A control system includes a programmable microprocessor which can be programmed to provide drain and flush cycles of predetermined duration. A method of liquid waste disposal and canister flushing utilizes the microprocessor for delaying the flush cycle until completion of the drain cycle. The control system can provide drain and flush cycles of predetermined durations, can monitor water pressure, flow rate and temperature, cleaning solution flow rate and other system parameters.

20 Claims, 13 Drawing Sheets

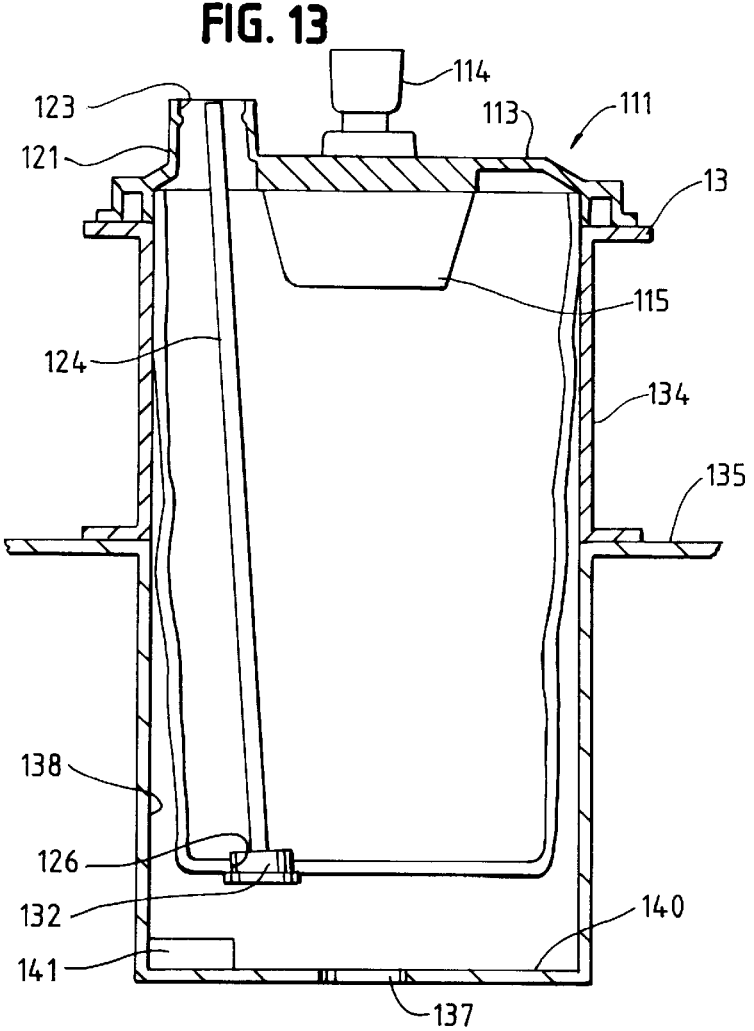
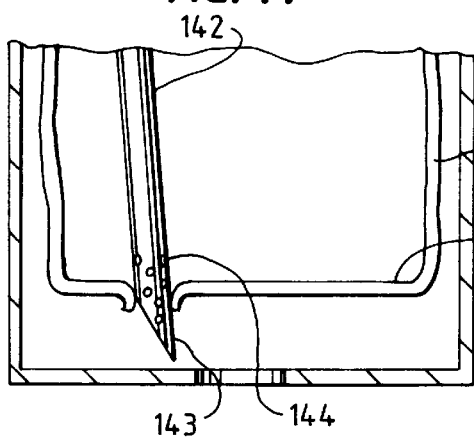
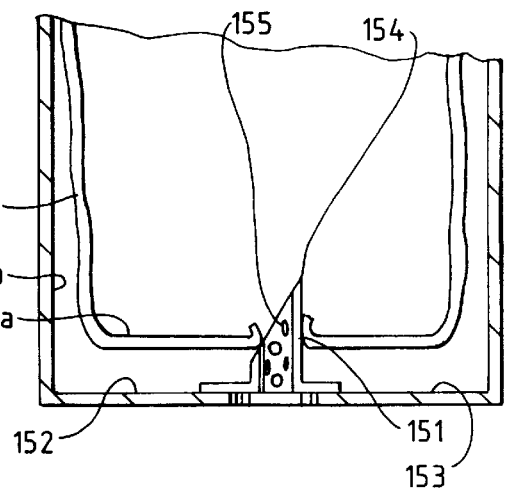

LIQUID WASTE DISPOSAL AND CANISTER FLUSHING SYSTEM AND METHOD

CROSS REFERENCE TO RELATED APPLICATIONS

This application is a continuation in part of application Ser. No. 08/698,940, entitled LIQUID MEDICAL WASTE DISPOSAL AND CANISTER FLUSHING SYSTEM AND METHOD, filed Aug. 16, 1996 now U.S. Pat. No. 5,776,260.

BACKGROUND OF THE INVENTION

I. Field of the Invention

The present invention relates generally to liquid waste disposal and canister flushing, and in particular to the disposal of liquid medical waste from containers which are flushed in preparation for reuse.

II. Description of the Related Art

Various forms of liquid waste are commonly encountered in a variety of different situations. For example, liquid medical wastes are commonly produced in surgery and other medical procedures. Such wastes can include blood and other body fluids of patients, and major surgery can produce a number of containers of such waste from a single patient. Liquid medical waste generates significant disposal problems due to its possible contamination with various infectious diseases, including AIDS, hepatitis, MRSA and tuberculosis. In an effort to combat the risks associated with handling such liquid medical wastes and to protect medical personnel from the spread of infectious diseases, disposal procedures have become increasingly complicated and expensive.

One type of disposal procedure for liquid medical wastes involves emptying the waste canisters from surgery into specially designed plumbing fixtures. However, this procedure can involve risks associated with splash back and aerosolization whereby medical personnel can be exposed to the waste and bacteria present therein.

Another type of procedure involves the centralized collection of the waste with specially designed equipment having a liquid waste reservoir that must periodically be dumped. Such equipment is generally relatively expensive and can add significantly to the cost of equipping a hospital operating room or other treatment facility.

Yet another method of disposing of liquid medical waste involves mixing it with a solidifying agent in the container. The medical waste in the container then disposed of pursuant to regulations governing the disposal of bio-hazardous waste. The disadvantages with this disposal method include the cost of the canister, which becomes a single-use item, and the extra charges for disposing of bio-hazardous waste, which is sometimes referred to as "red bag" waste.

Liquid medical waste disposal procedures can come under rules and regulations imposed by various governmental and regulatory agencies, including the Occupational Safety and Health Administration (OSHA), the Food and Drug Administration (FDA), and the Center for Disease Control (CDC).

Heretofore there has not been available a liquid medical waste disposal system and method with the advantages and features of the present invention.

SUMMARY OF THE INVENTION

In the practice of the present invention, a liquid waste disposal and canister flushing system is provided which includes a cabinet forming a sink with one or more subsinks for receiving a bottom portion of a waste canister. The subsink(s) are connected to a drain line. In a first embodiment, each canister includes a lid with an accessory opening, a base with a drain opening, and a sidewall connected to the lid and to the base. With a lower portion of the canister received in the subsink, the canister base is positioned above a bottom of the subsink. A plunger assembly includes a stopper positioned in the canister base drain opening for closing same and a rod with a lower end connected to the stopper and an upper end positioned in the canister lid accessory opening. An injection jet is connected by water and cleaning solution lines to water and cleaning solution sources and mixes water and cleaning solution, such as bleach, to form a diluted cleaning solution which is discharged therefrom into the canister. The injection jet is inserted in the canister lid accessory opening where it engages the plunger subassembly rod upper end and ejects the stopper into the subsink, thus opening the drain valve and permitting the liquid waste contents of the canister to drain into the subsink and then into the drain line. When the drain cycle is complete, the diluted cleaning solution is discharged from the injection jet into the canister for flushing same. A control system is provided for sequencing the drain and flush cycles whereby the flush cycle does not commence until the drain cycle is complete. The control system can include a programmable microprocessor which allows the drain and flush cycle durations to be adjusted, provides visual and audio indications of the status of the system in operation and which prevents flushing until the canisters are enclosed in the sink with a lid of the cabinet closed. Other functions which can be monitored and/or controlled by the microprocessor include water pressure for flushing, titration flow control of bleach to achieve desired cleaning solution/flush water ratios, monitoring of ratio of amount of liquid waste to volume of flush water, monitoring of water temperature, and storing and archiving of any exceptions to desired parameters and automatic shut-off of the system when parameters exceed a predetermined level. The cabinet can be equipped with lid locking solenoids to eliminate splash risk and the microprocessor can monitor the lid lock condition to prevent flushing operation when the lid is not locked down. An on-board modem can be provided for remote monitoring and emergency paging functions and an on-board LCD display can be provided for instantaneous feedback of system conditions.

A method of disposing of liquid waste and flushing a canister containing same is also provided and consists of the steps of draining the canister for a predetermined time prior to commencement of a flush cycle and flushing the canister for a predetermined time interval corresponding to a flush cycle.

In a first alternative form of canister, a reusable, rigid outer casing is used with a disposable flexible inner liner. The flexible liner, which is too flexible to be self-supporting, is preferably sonically welded to a lid with a plurality of upper openings, including an accessory opening. The liner is also equipped with a bottom opening closed by a removable stopper and includes a plunger rod extending between the accessory opening and the stopper. The rigid outer casing has a bottom opening, which can be closed by a stopper which is preferably manually removed prior to placement in the cabinet, and which is sized to rest partially in a subsink in the cabinet, as described above. The injection jet is then inserted into the accessory opening, pushing the plunger rod downward to force the bottom stopper out of the liner. Any contents of the liner then drain out of the liner, out of the bottom opening in the casing and out of the subsink. Flushing and disinfecting is accomplished as described above. The flexible liner is disposable while the casing is reusable. The lid of the flexible liner, the outer casing, and, optionally, the subsink, can all be keyed such that a correct relative orientation is assured.

In a second alternative embodiment of canister, a semi-rigid container is provided whose composition resembles a plastic milk carton, i.e. it is rigid enough to be self supporting. As in the flexible liner, the semi-rigid container is also preferably sonically welded to a lid with a plurality of upper openings, including an accessory opening. The liner is also equipped with a bottom opening closed by a removable stopper and includes a plunger rod extending between the accessory opening and the stopper. While the semi-rigid liner can be positioned inside a rigid outer casing for transport, it is preferably designed for stand alone use with a special subsink in the cabinet. The special subsink has a perimeter wall which extends upward from the bottom of the sink and is sized to engage the lid of the semi-rigid container such that the subsink itself serves to support and surround the semi-rigid container during flushing and disinfecting operations. Again, as described above, once the semi-rigid container is in position in the subsink, the injection jet is inserted into the accessory opening, pushing the plunger rod downward to force the bottom stopper out of the container. Any contents of the container then drain out of the container and out of the subsink. Flushing and disinfecting is accomplished as described above. The flushed and disinfected container can then be disposed of with ordinary refuse.

In a first alternative flushing arrangement, the bottom opening of the semi-rigid container can be eliminated and the internal plunger rod can have a sharp point, shaped as a trocar. When the plunger rod is forced downward by the flush jet, the trocar punctures the container bottom, thus allowing the fluid to drain therefrom. In a second alternative flushing arrangement, the internal plunger rod in the semi-rigid container can be eliminated and an upstanding plunger rod affixed to the bottom of the subsink, partially surrounding the subsink drain. The upstanding plunger rod can be equipped with a trocar point which punctures the bottom of the semi-rigid container when it is positioned in the subsink, thus causing it to drain. In either case, flushing and disinfecting are accomplished as described above, and the punctured semi-rigid container can be disposed of with ordinary refuse.

In either embodiment of flexible liner or semi-rigid container, the accessory opening can be shaped as an inverted funnel, which acts as a guide for the internal plunger rod during insertion and draining operations. The bottom drain opening in the rigid containers and the flexible liners and semi-rigid containers can be filleted around the edges to eliminate sharp edges and to facilitate complete drainage. The accessory opening can include an inside perimeter ridge which allows the flush jet to be snapped into position thereon.

OBJECTS AND ADVANTAGES OF THE INVENTION

The principal objects and advantages of the present invention include: providing a liquid waste disposal and canister flushing system; providing such a system which facilitates the relatively inexpensive disposal of medical waste; providing such a system which facilitates reuse of medical waste containers; providing such a system which is relatively easily adapted for use with existing medical waste containers; providing such a system which reduces the splashing of medical waste being disposed; providing such a system which can reduce the hazards associated with handling and disposing of medical waste; providing such a system which facilitates the discharge of medical waste into a sewer system; providing such a system which can reduce the amount of disposable components associated with medical waste disposal; providing such a system which provides effective neutralization of various bacteria and infection sources; providing such a system which is usable by medical personnel with relatively little training; providing such a system with a control system which is at least partially automated; providing such a system which is relatively portable; providing such a system which is relatively compact; providing such a system which can be installed with relatively simple plumbing and electrical connections; providing such a system which is economical to manufacture and use, efficient in operation, capable of a long operating life and generally well adapted for the proposed usage thereof; providing a liquid medical waste disposal and canister flushing method; providing such a method which is relatively efficient; providing such a method which is relatively safe; providing such a method which is relatively economical and providing such a method which is particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 13 is a cross-sectional view of a second embodiment of canister including a semi-rigid container with an internal plunger rod and bottom opening inserted into a modified subsink.

FIG. 14 is a fragmentary, cross-sectional view of a modified version of semi-rigid container, including an internal plunger rod with a sharp point designed to puncture the container bottom from within upon insertion of a flush jet.

FIG. 15 is a fragmentary, cross-sectional view of another modified version of semi-rigid container, including an internal plunger rod extending upward from around the drain opening of the subsink and also equipped with a sharp point designed to puncture the container bottom from without once the container is properly seated in the subsink.

DETAILED DESCRIPTION OF THE INVENTION

Figure 1:
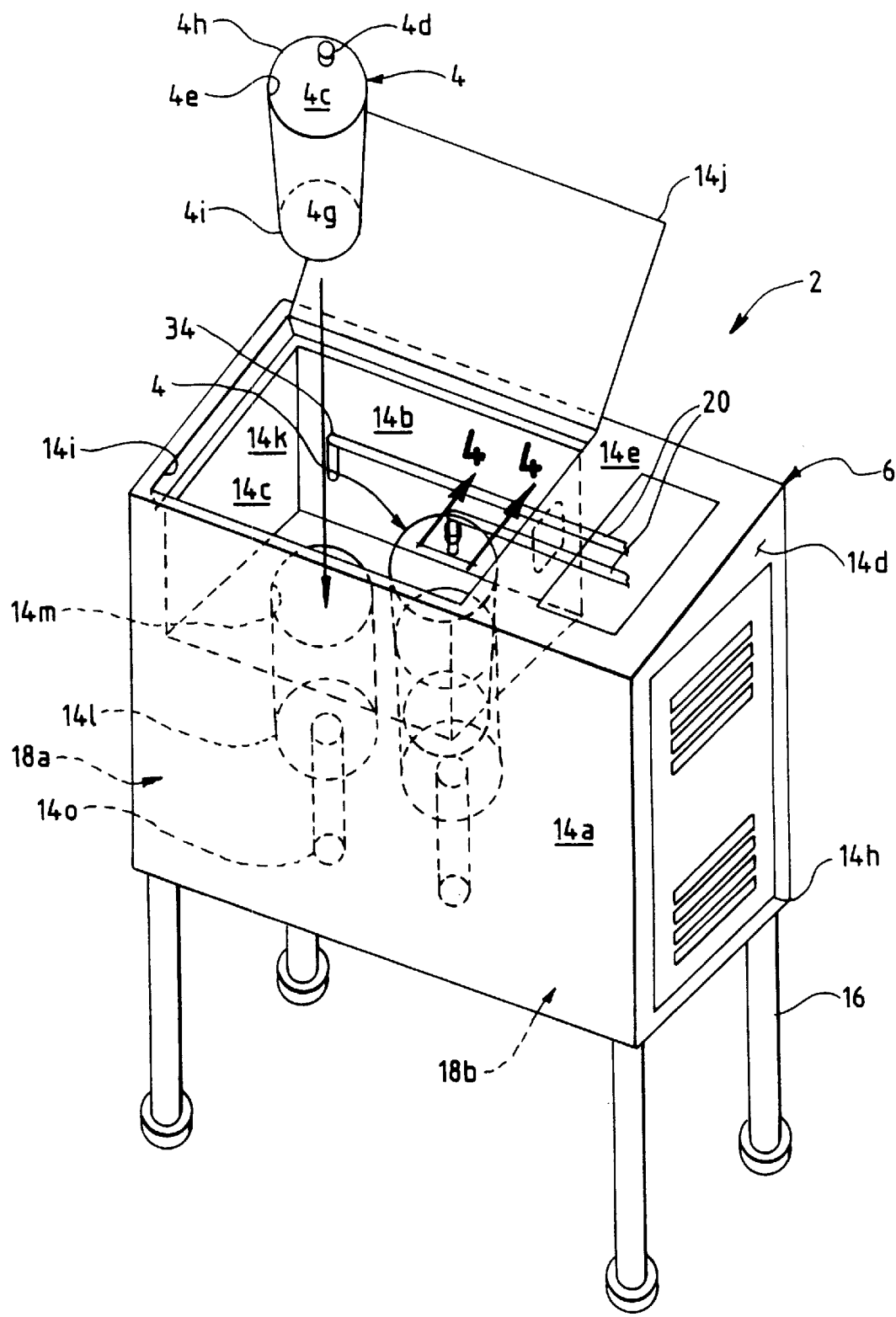
FIG. 1 is an upper, front perspective view of a liquid medical waste disposal and canister flushing system embodying the present invention.
Figure 2:
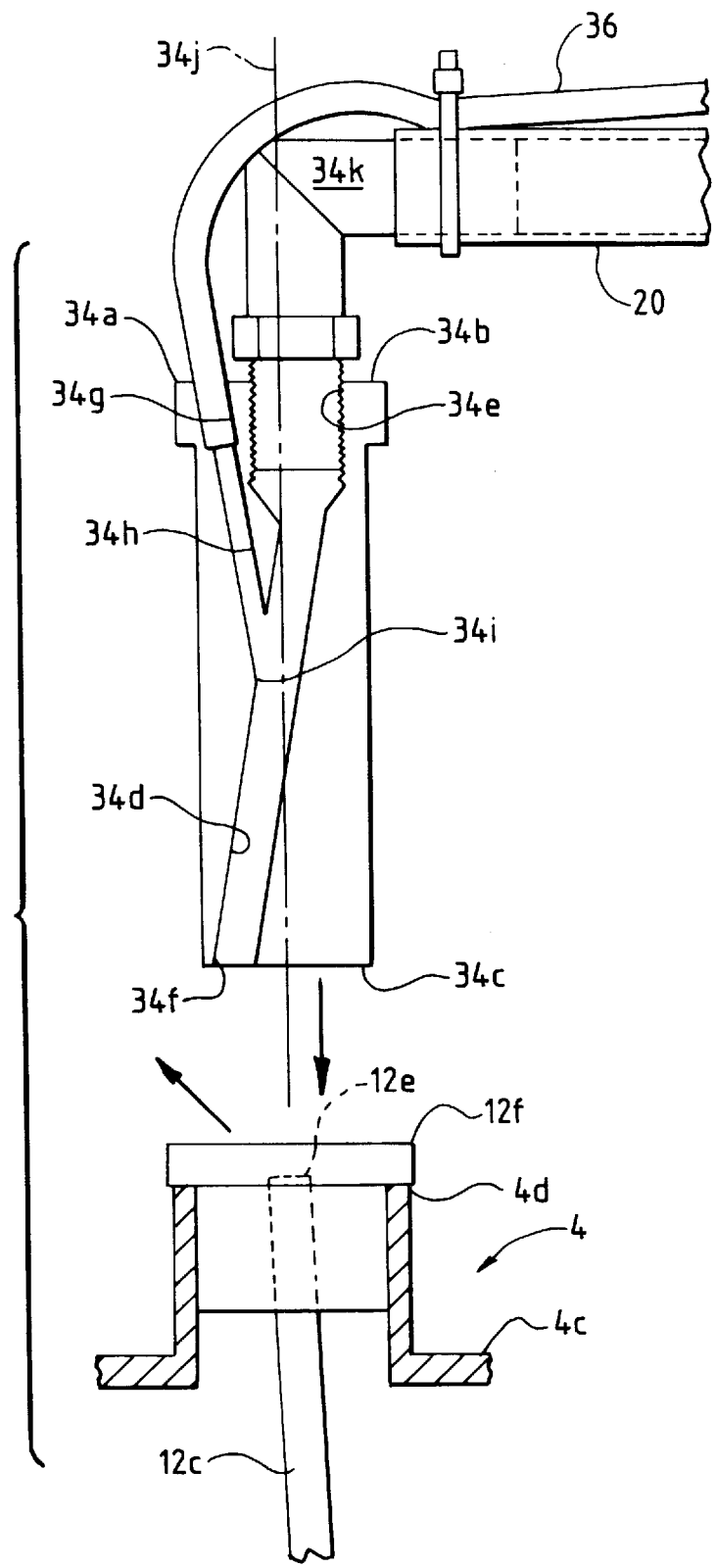
FIG. 2 is an enlarged, fragmentary, vertical cross-sectional view thereof.
Figure 3:
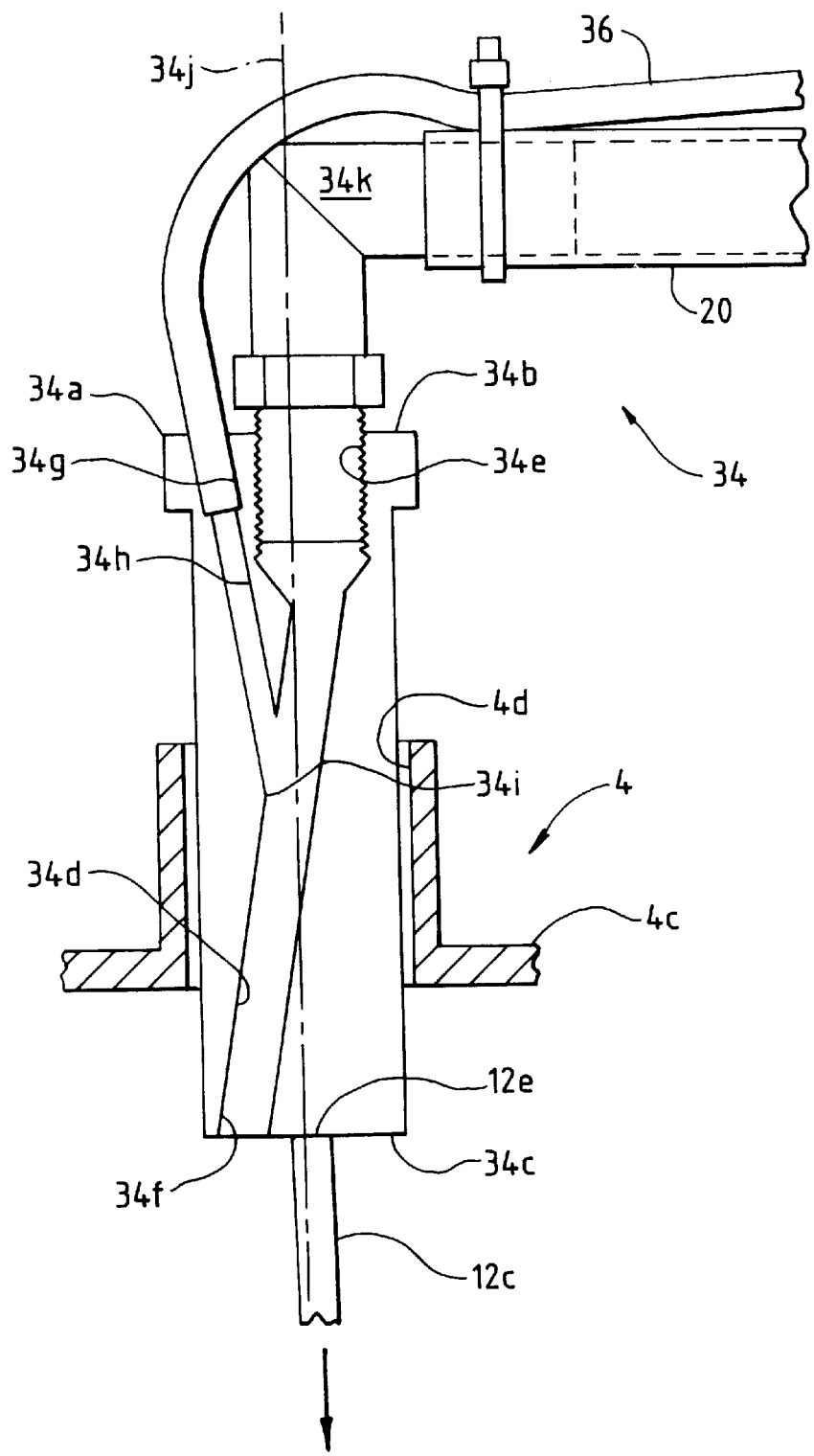
FIG. 3 is an enlarged, fragmentary, vertical cross-sectional view thereof, showing an injection jet being inserted into a canister lid and dislodging a plunger subassembly.
Figure 4:
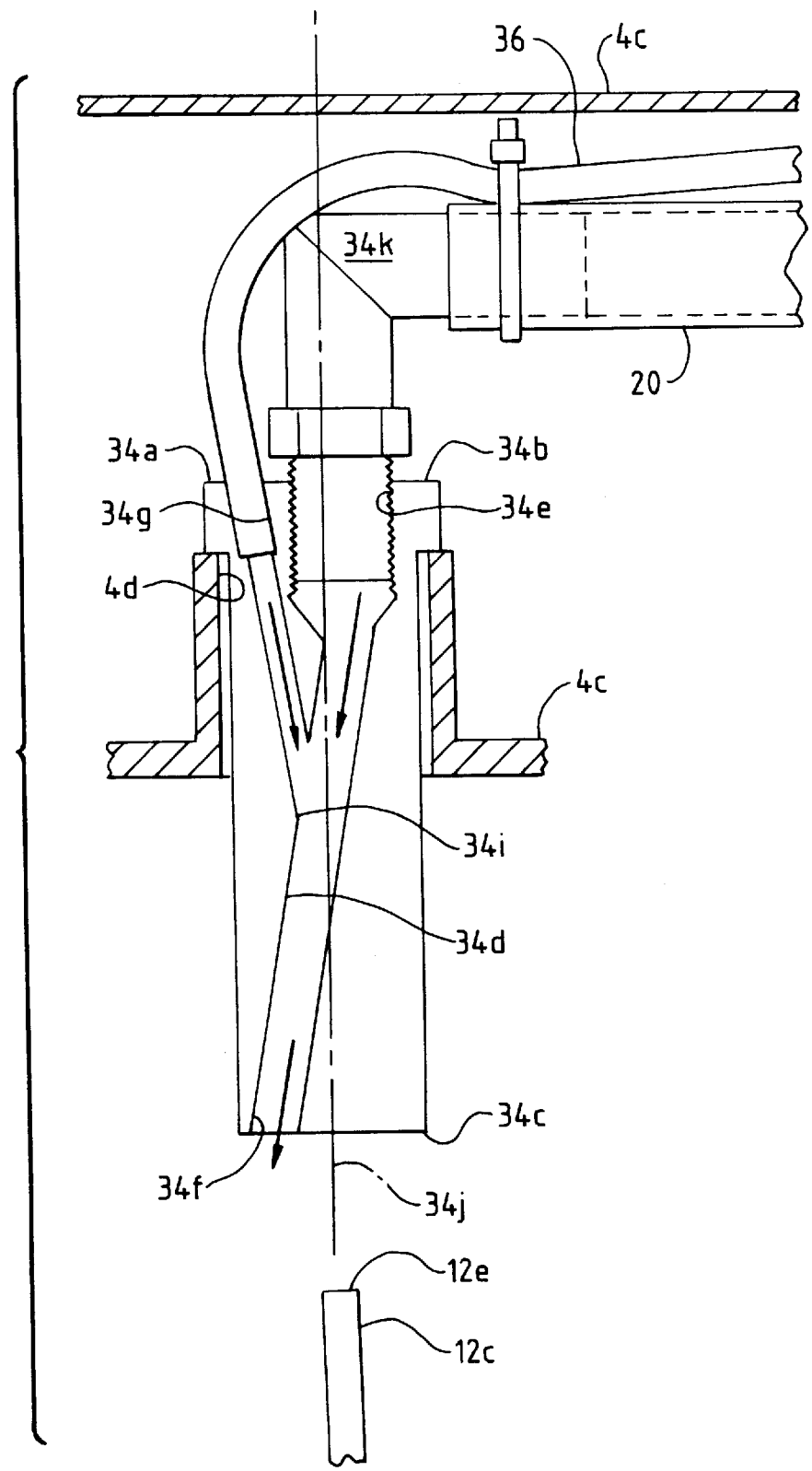
FIG. 4 is an enlarged, fragmentary, vertical cross-sectional view thereof, taken generally along line 4—4 in FIG. 1 and showing an injection jet inserted in the lid of one of the canisters.
Figure 5:
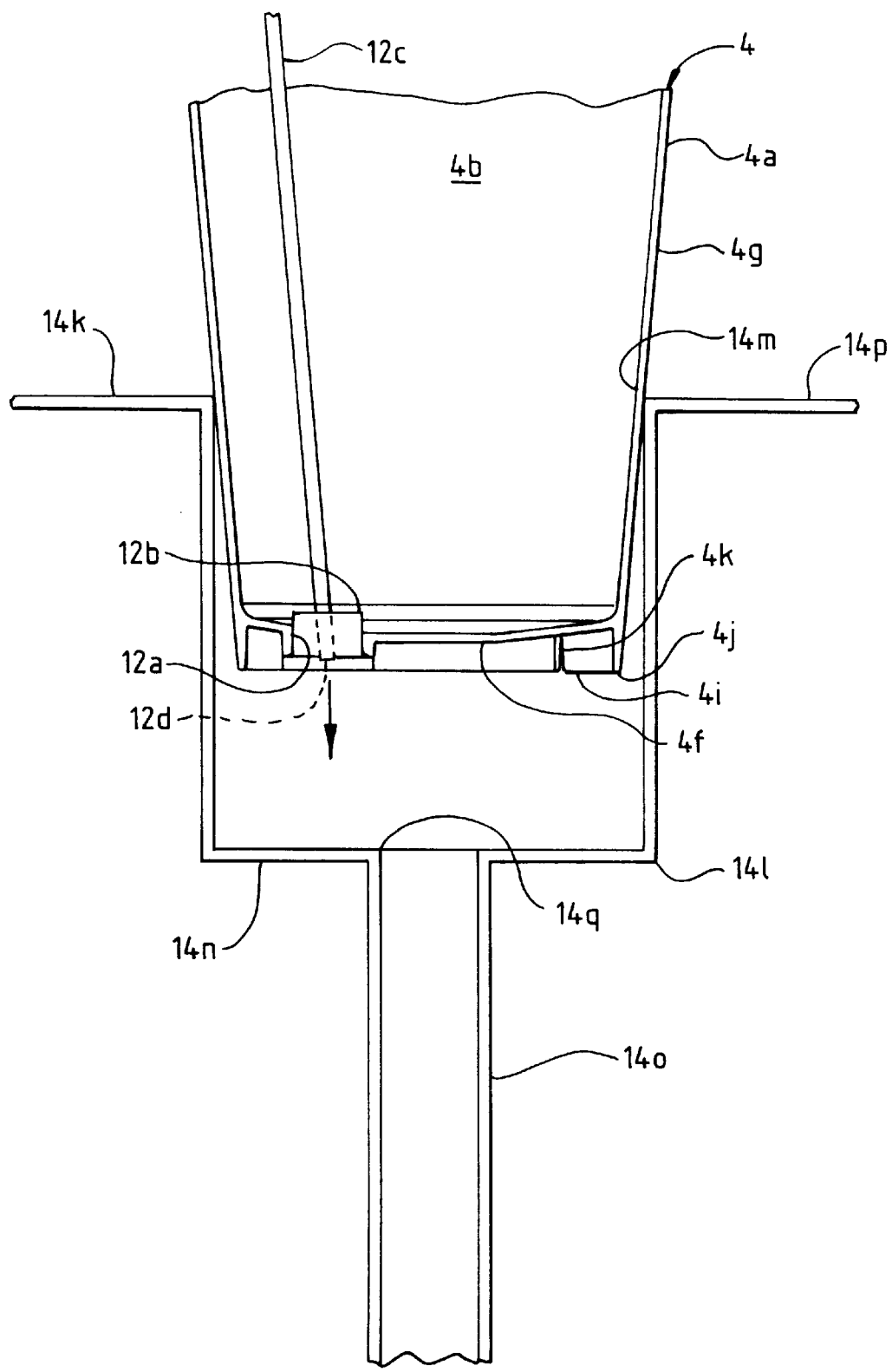
FIG. 5 is an enlarged, fragmentary, vertical cross-sectional view thereof, generally showing a lower end of the canister positioned in a subsink with the plunger subassembly in a closed position.
Figure 6:
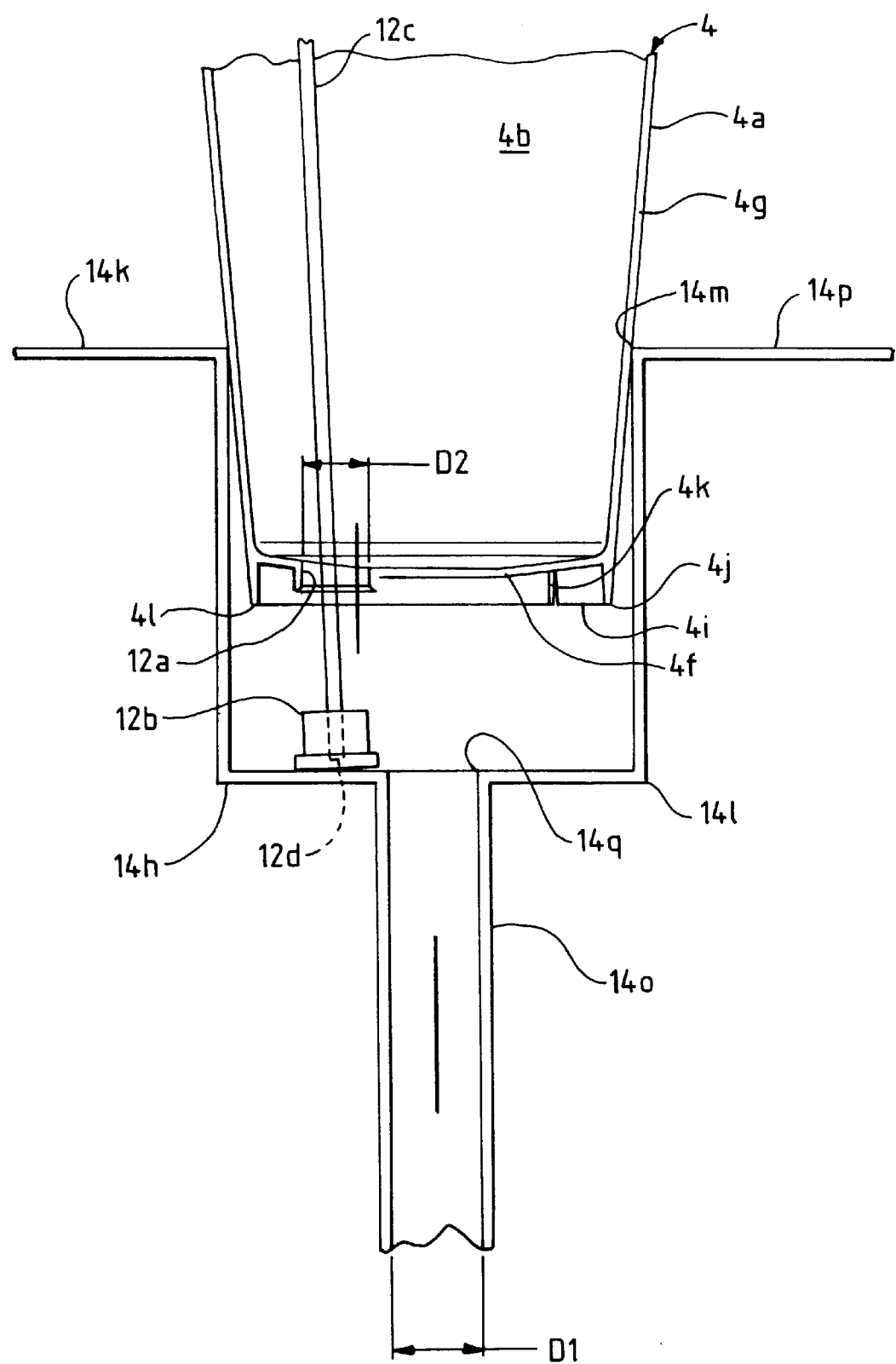
FIG. 6 is an enlarged, fragmentary, vertical cross-sectional view thereof, generally showing a plunger subassembly in an open, drain position.
Figure 7:
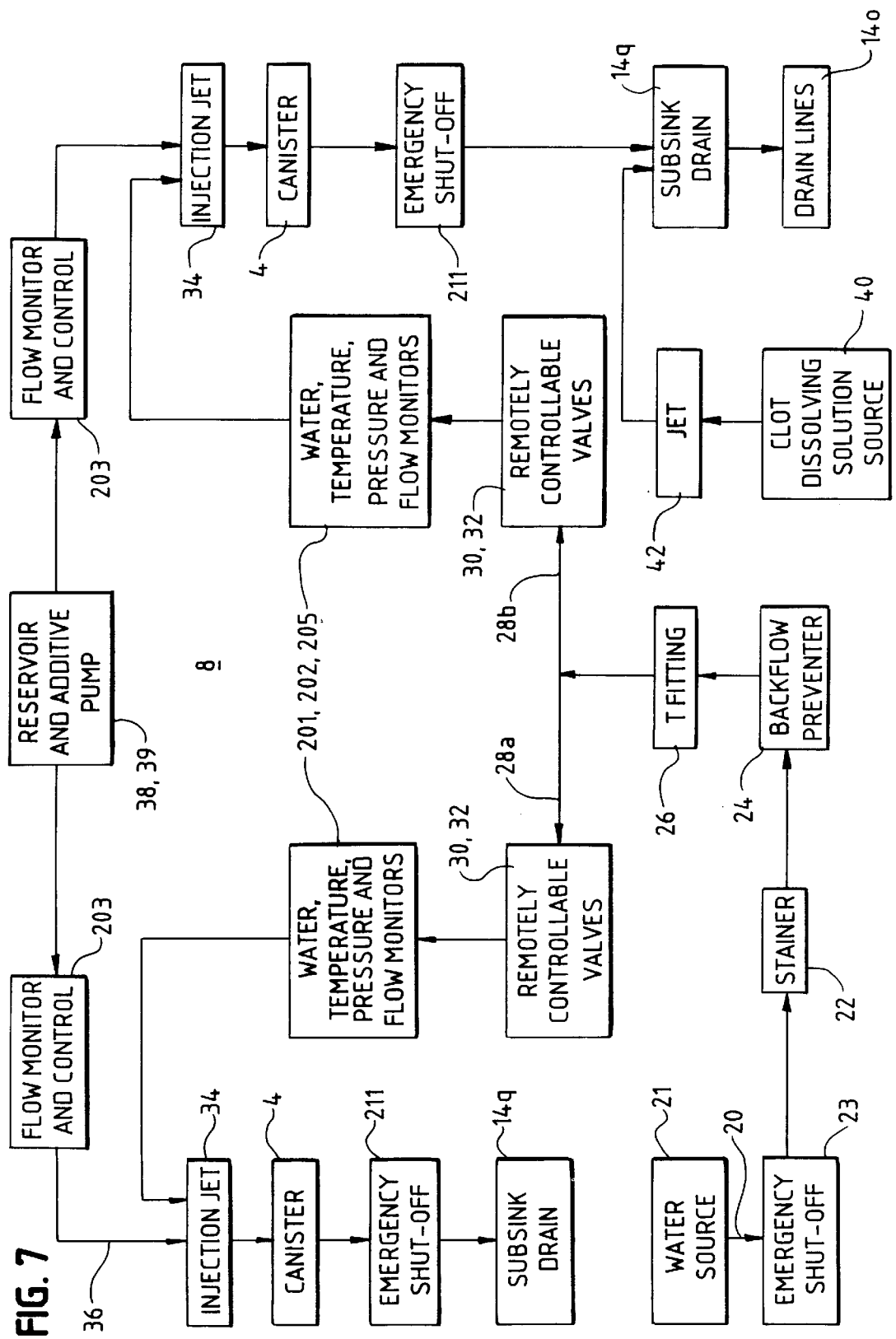
FIG. 7 is a schematic diagram of a plumbing system thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 2 generally designates a liquid medical waste disposal and canister flushing system embodying the present invention. Without limitation on the generality of useful applications of the system 2, it is designed for operation on modified medical waste canisters 4. The system 2 generally comprises a cabinet 6, a plumbing system 8 and a control system 10.

II. Canister 4

An exemplary application of the disposal and flushing system 2 is with a canister 4 of the type which is commonly used in surgery for medical waste generally comprising the patient's blood and other fluids. A typical such canister is available from Allied Healthcare Products, Inc. of St. Louis, Mo. and includes a body 4a forming a receptacle 4b of predetermined volume (e.g. 2550 milliliters) and a releasable lid 4c which is preferably upwardly-convex to prevent the pooling of fluids thereon. The body 4a includes upper and lower ends 4h,i. The lid 4c can be secured to the body 4a with a Leur lock-type connection and can include suitable inlet ports, fittings for vacuum lines, check valves, clamps, etc. The lid 4c includes an accessory port 4d with a generally cylindrical, tubular configuration and an open mouth 4e. The canister 4 further includes a base 4f, which is generally circular, and a frusto-conical sidewall 4g which converges downwardly in a tapering configuration to permit nesting of canister bodies 4a.

The canister 4 described thus far is a relatively standard configuration. For use with the system 2 of the present invention, the standard canister 4 is modified to include a plunger subassembly 12 for which a drain opening 12a is formed off-center in the canister base 4f and selectively receives a stopper 4b in sealing engagement. The canister base 4f is provided with a configuration which is concave from the inside of the canister and to facilitate drainage through the drain opening 12a, which opens at approximately the lowest level of the concave base 4f. A canister bottom flange or lip 4j extends downwardly from the canister base 4f and comprises an extension of the canister sidewall 4g. A plurality of drain notches 4k are formed in the bottom lip 4j and cooperate with the concave configuration of the canister base 4f whereby water will drain from the canister base 4f with the canister 4 in an inverted position, for example, when automatic dishwashing equipment is used for washing the canisters 4 in inverted positions.

A plunger rod 12c includes a lower end 12d embedded in the stopper 12b and an upper end 12e protruding into the accessory port 4d and mounting an upper cap 12f which is received in and is adapted to selectively close the accessory port 4d. In addition to the plunger subassembly 12 shown, other drain valve means can be utilized with the canister 4. These can include, for example, a variety of caps, lids, plugs and spring loaded devices for selectively opening and closing a drain opening formed in either the canister base 4f or the canister sidewall 4g.

III. Cabinet 6

The cabinet 6 includes front and back panels 14a,b; first and second side panels 14c,d; and a top 14e. The second side 14d has an opening which is selectively covered by a side access panel 14h. A top opening 14i is selectively covered by a lid 14j hingedly mounted on the top panel 14e. The top opening 14i provides access to a sink 14k. A pair of subsinks 14l with open, upper mouths 14m and subsink bottoms 14n depend downwardly from a floor 14p of the sink 14k. The subsinks 14l are generally cylindrical. Although two subsinks 14l are shown, the system 2 could include a single subsink 14l or more than two subsinks 14l. The subsinks 14l communicate through subsink drain openings 14q in their bottoms 14n with subsink drain lines 14o comprising the plumbing discharge subsystem 8b. The cabinet 6 is provided with adjustable-length legs 16 for leveling. An interior 18 of the cabinet 6 generally forms a sink chamber 18a and a control chamber 18b.

IV. Plumbing System 8

The plumbing system 8 generally includes a supply subsystem 8a and a drain subsystem 8b. The supply subsystem 8a includes a water inlet line 20 connected to a suitable pressurized water source 21, such as the normal municipal water service, a water tank or a water pump. A strainer 22 is provided in the water inlet line 20 and a backflow preventer valve 24 is provided downstream therefrom. The water inlet line 20 connects to a T-fitting 26, forming first and second supply branches 28a,b.

Each supply subsystem branch 28a,b includes a gate-type shut-off valve 30 and a solenoid-actuated valve 32 in line therewith. Each water inlet line 20 terminates in an injection jet 34, which also communicates with a cleaning solution injection line 36 communicating with a cleaning solution source 38, which can include a pump 39 for pumping the cleaning solution under pressure to the injection jet 34.

Each injection jet 34 includes a generally cylindrical body 34a with a flanged upper end 34b and a lower end 34c. A jet passage 34d extends downwardly from a threaded water inlet port 34e located off-center in the upper end 34b. The water inlet line 20 is connected to the water inlet port 34e by an elbow 34k. A discharge orifice 34f is located in the body lower end 34c, and is also off-center whereby the jet passage 34d is skewed with respect to a longitudinal axis 34j of the injection jet body 34a. Due to the skewed, angular orientation of the jet passage 34d, diluted cleaning solution therefrom is directed generally at the canister sidewall 4g, creating a swirling flushing action in the canister receptacle 4b. A cleaning solution inlet port 34g is formed in the body upper end 34*b* and communicates with a cleaning solution passage 34*h* which forms a Y-intersection 34*i* with the jet passage 34*d* in an interior part of the body 34*a*. The cleaning solution inlet port 34*g* is connected to the cleaning solution line 36.

A venturi effect is created by passage of water through the jet passage 34*d* whereby cleaning solution is drawn through the cleaning solution passage 34*h* for combining with water to form the diluted cleaning solution mixture which is discharged through the discharge orifice 34*f*.

An optional clot-dissolving solution source 40 communicates with a drain line jet 42 directed into the drain line 14*o* and functions to dissolve blood clots therein. Although the clot-dissolving solution source 40 and the jet 42 are optionally shown on the second plumbing system branch 28*b*, they could be provided on the first branch 28*a* as well, or eliminated all together whereby clots in the drain line 14*o* could be dealt with manually.

V. Control System 10

The control system 10 utilizes a control microprocessor 50. A program port 52 provides input access to the microprocessor 50 through a suitable RAM device 53*a*. A ROM device 54 is also connected to the microprocessor 50.

Analog-to-digital input conversion capabilities are provided by an A\D convertor 56 which is connected to an encoder 58, which in turn is connected to the microprocessor 50 through a RAM device 53*b*. A selection key 60 also provides digital input to the encoder 58. A level probe 62 is connected to the solution source 38 for monitoring the level therein and is connected to the RAM device 53*b* through an amplifier 62*a*.

A solenoid valve control 64 includes a digital output module 64*a* which is connected to the solenoid valves 32 and to a pair of indicator lights 64*b* for indicating the open or closed positions of the solenoid valves 32. The digital output module 64*a* is connected to the microprocessor 50 through a RAM device 53*c*.

A display device 66 is mounted on the cabinet top panel 14*e* and is connected to the microprocessor 50 through a RAM device 53*d* and a driver 66*a* and can comprise, for example, an LED or LCD display for indicating the state of the control system 10 or various functions thereof, such as time remaining to complete a flush cycle, delay mode (as explained in more detail below), etc.

Figure 8:
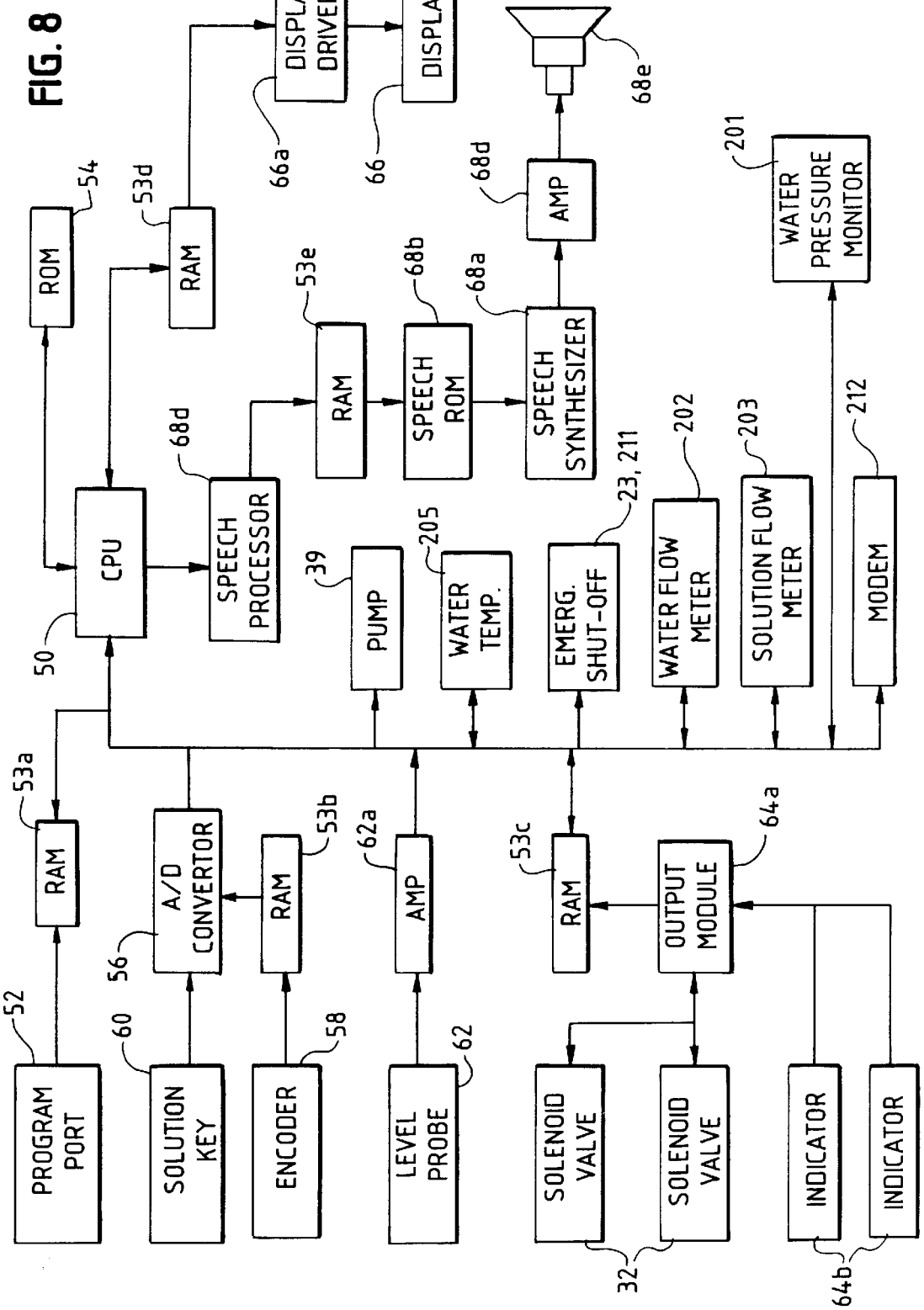
FIG. 8 is a schematic diagram of a control system thereof.

A voice enunciation subsystem 68 includes a speech synthesizer 68*a* connected to the microprocessor 50, a RAM device 53*e*, a speech ROM device 68*b*, an amplifier 68*d* and a suitable output device, such as a speaker 68*e*, all suitably interconnected as shown in FIG. 8. A water pressure sensor 201 is connected to the microprocessor 50 for monitoring water pressure to insure that it is adequate. A water flow sensor 202 and an additive flow sensor 203 monitor fluid flow to allow titration of the additive and flow of water to be monitored to calculate concentration of additive (cleaning solution) in the water. The microprocessor 50 thus controls valves 32 and the pump 39 to achieve the desired additive concentration. Monitoring of water flow by the microprocessor 50 insures compliance with government regulations. A water temperature monitor 205 allows the microprocessor 50 to monitoring of water temperature. A remotely controlled emergency shut-off 23 and 211 allows the microprocessor 50 to shut off the drain of the cabinet 6 as well as all fluid inputs in the event that monitored parameters are outside of predetermined limits. The microprocessor 50 also stores and archives of any exceptions to desired parameters. An optional modem 212 can be provided for remote monitoring and emergency paging functions for the on-board display 66 can be provided for instantaneous feedback of system conditions.

It will be appreciated that the control system 10 can comprise various alternative configurations with appropriate analog, digital or analog/digital components for controlling various functions of the system 2. In particular, other inputs and outputs could be provided for monitoring various functions of the system 2 and for automating same to a greater or lesser degree.

VI. First Alternative Embodiment of Canister 71

Figure 10:
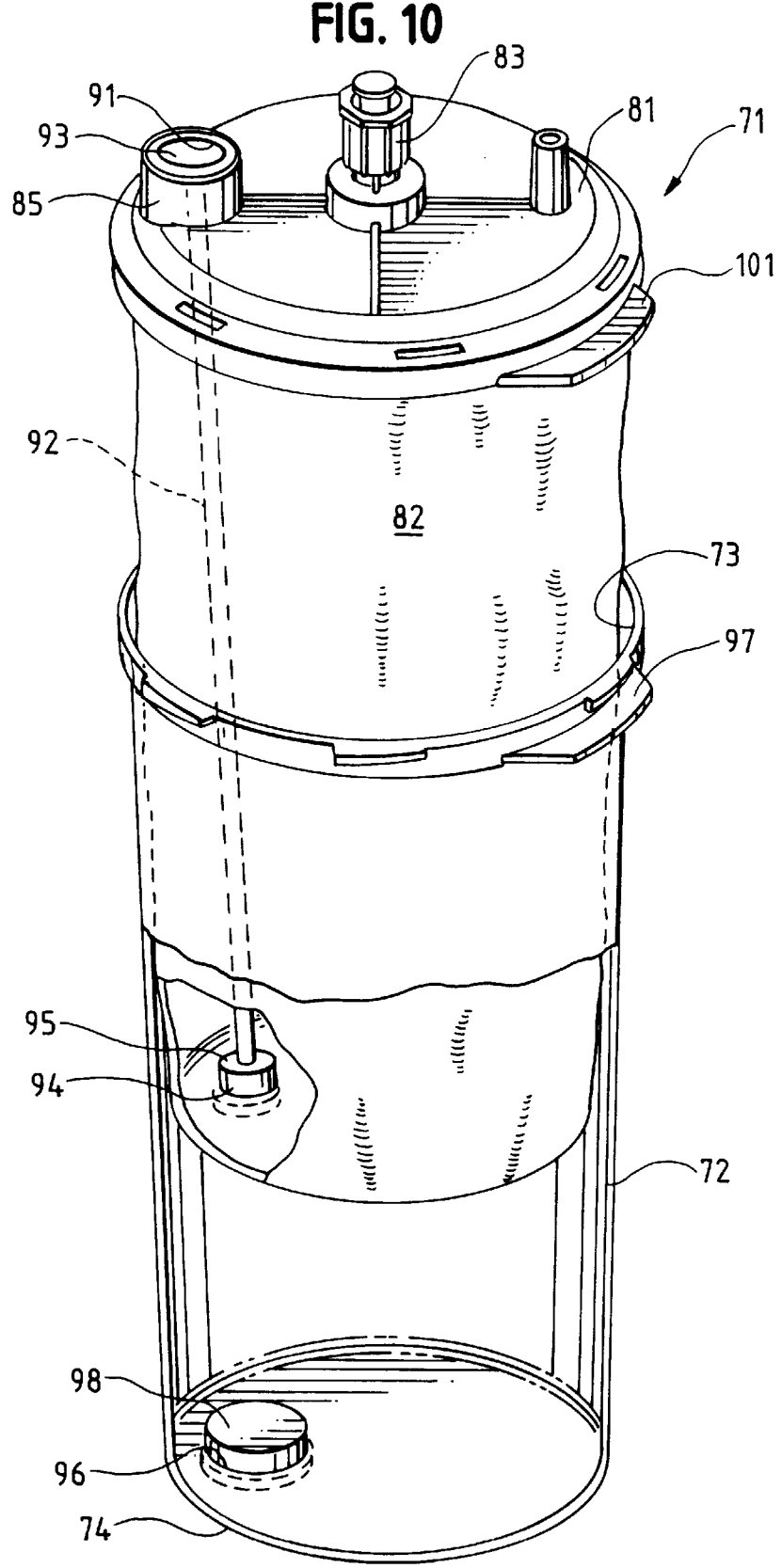
FIG. 10 is a perspective view of a first alternative embodiment of canister with disposable flexible liner.
Figure 11:
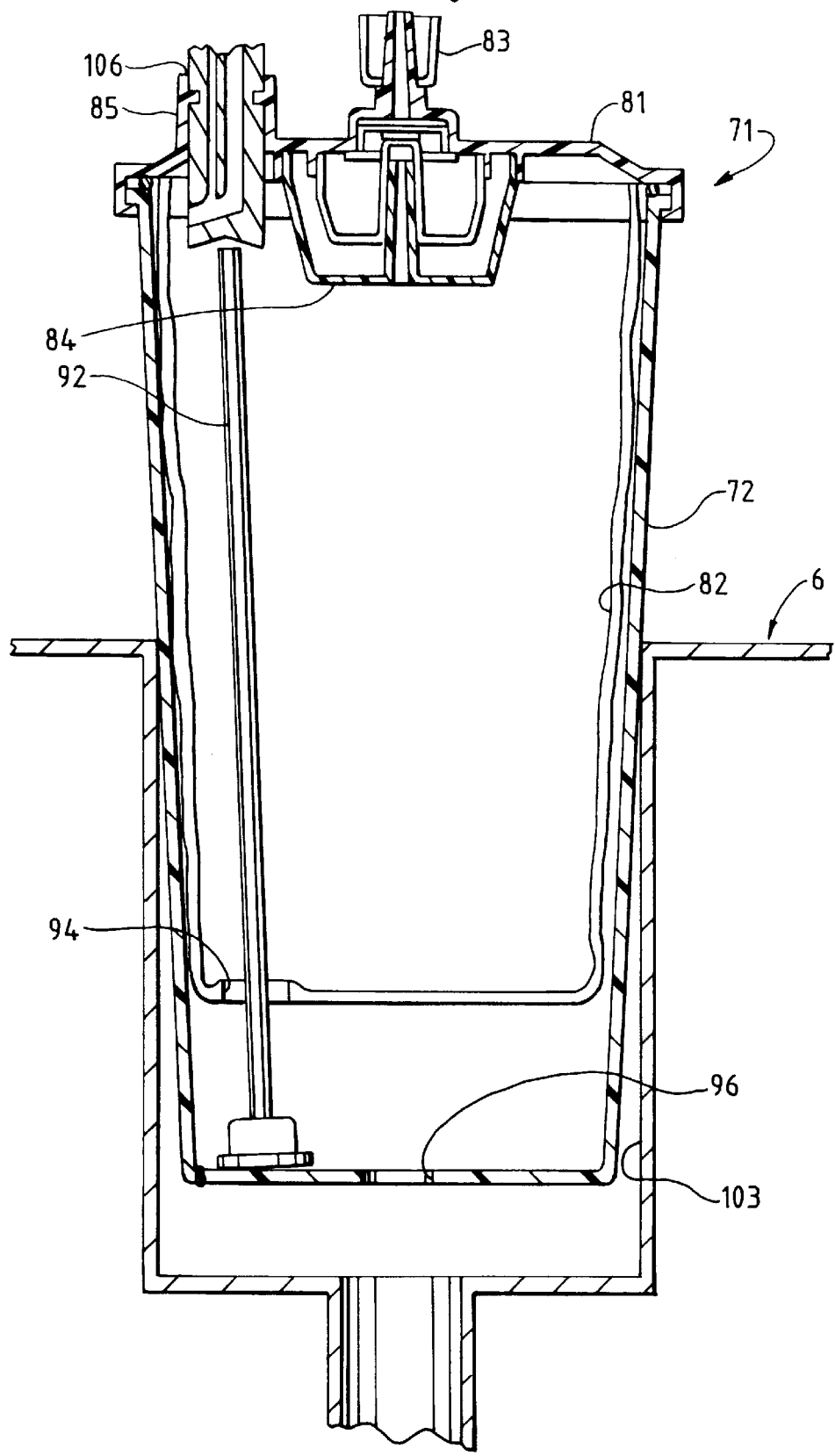
FIG. 11 is a cross-sectional view of the container of FIG. 10, positioned in a subsink in a cabinet and with a flush jet inserted into position for flushing and disinfecting.

Referring to FIGS. 10 and 11, a first alternative embodiment of canister is generally indicated at 71. The canister 71 includes a rigid outer casing 72 with perimeter walls which preferably form a frusto-conical shape extending from a generally circular open top 73 to a smaller diameter, generally circular closed bottom 74. The rigid casing 72 can be similar to the canister 4 described earlier, and can include a Leur lock-type connection 75 at the open top 73 to accommodate a releasable lid 81 which is, again, preferably upwardly-convex to prevent the pooling of fluids thereon. The lid 81 is sonically welded to a flexible liner 82 and includes a fitting 83 for a vacuum line with an internal check valve 84. The lid 81 also includes an accessory port 85 which opens into the interior of the flexible liner 82. The port 85 is shaped with generally cylindrical, tubular configuration, and can include at least one sloping wall 86 which resembles an inverted funnel, and an open mouth 91.

A plunger rod 92 is attached to a plug 93 which covers and seals the open mouth 91 of the port 85. The sloping wall 86 acts as a guide for the plunger rod as it is inserted into the liner 82. A drain opening 94 is formed in the bottom of the flexible liner 82, and the drain opening 94 can be reinforced to hold a removable stopper 95 which is engaged by the plunger rod 92. The closed bottom 74 of the rigid casing 72 includes a drain opening 96 which can be beneath (FIG. 10) or offset from (FIG. 11) the drain opening 94 in the flexible liner 82. In order to assure proper alignment of the liner 82 and the outer casing 72, an optional ovate key extension 97 can be included in the open top 73 of the casing 72, which key extension 97 mates with a similar, optional extension 101 in the lid 81 when the liner 82 is properly aligned in the casing 72. The bottom 74 of the casing 72 is preferably provided with a concave upper surface to facilitate drainage through the drain opening 95. An optional removable stopper 98 similar to the stopper 95 is positionable in the drain opening 96, which stopper 98 is preferably removed prior to insertion of the casing 71 in a subsink 103 of the cabinet 6, as shown in FIG. 11. The drain opening 95 can have filleted edges 99 to minimize sharp surfaces.

Figure 12:
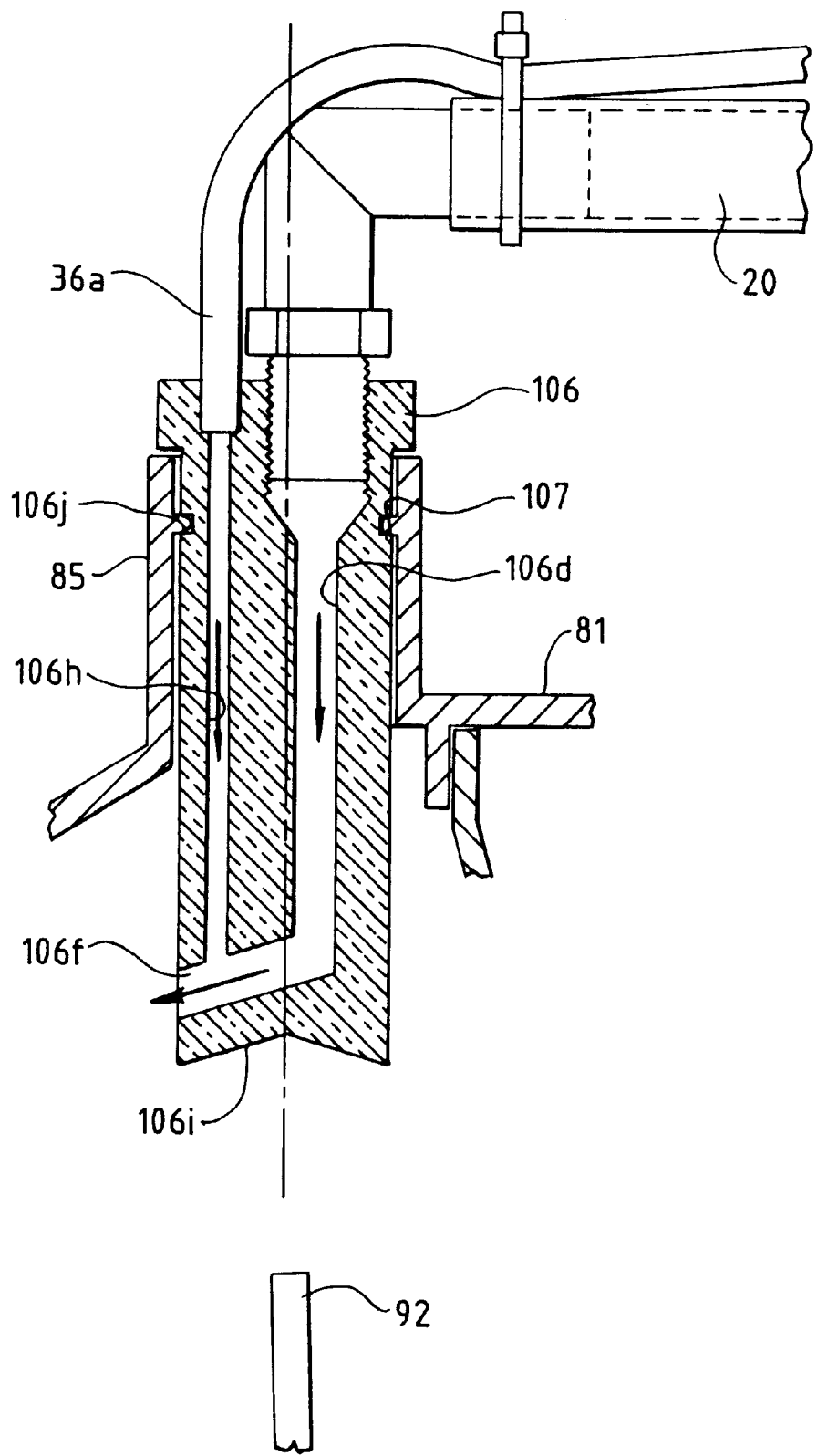
FIG. 12 is a greatly enlarged, cross sectional view of a modified flush jet fitting designed to eliminate any venturi effect between water inlet and cleaning solution inlet.

The port 85 serves as a receptacle for a modified injection jet 106 (best illustrated in FIG. 12), which also communicates with a cleaning solution injection line 36*a*. The modified jet 106 is designed to eliminate any venturi effects created by passage of water through a jet passage 106*d* whereby cleaning solution pressure and flow can be accurately controlled solely by operation of a disinfectant pump (not shown in FIG. 11) attached to the cleaning solution passage 106*h* for combining with water to form the diluted cleaning solution mixture which is discharged through a discharge orifice 106*f*. The injection jet 106 also includes a beveled bottom surface 106*i* which accommodates a top of the plunger rod 92 to securely hold the plunger rod 92 as it is being forced downward by the jet 106. Again, by introducing the jet 106 into the port 85, the plunger rod 92 pushes the stopper 95 out of the drain opening 94, thus draining the flexible liner 82 and preparing the liner 82 and the casing 72 for flushing and disinfectant. The injection jet 106 can incorporate a perimeter slot 106j which mates with an interior perimeter ridge 107 in the port 85 to securely snap the injection jet 106 into position within the port 85.

VII. Second Alternative Embodiment of Canister 111

Referring to FIG. 13, a second alternative embodiment of canister is generally indicated at 111. The canister 111 comprises a semi-rigid container 112 which is preferably sonically welded to a lid 113. The lid 113 is similar to the lid 81, i.e. it is preferably upwardly-convex to prevent the pooling of fluids thereon and includes a fitting 114 for a vacuum line with an internal check valve 115. The lid 113 also includes an accessory port 121 which opens into the interior of the semi-rigid container 112. The port 121 is shaped with generally cylindrical, tubular configuration and an open mouth 123.

A plunger rod 124 is attached to a stopper 125 which covers and seals the open mouth 123 of the port 121. A drain opening 126 is formed in a bottom 131 of the semi-rigid container 112, and the drain opening 126 can be reinforced to hold a removable stopper 132 which is engaged by the plunger rod 124.

The canister 111 is designed to work with a modified subsink 133 which includes a cylindrical perimeter wall 134 which extends upward from a bottom surface 135 of the sink chamber 18a of the cabinet 6. The lid 113 has peripheral ledge which is sized to rest on an upper surface 136 of the subsink perimeter wall 134 in a position such that the drain opening 126 in the semi-rigid container 112 is positioned above a bottom surface 140 of the subsink 133. In order to minimize "swirl" of the drained contents of the container 112 in the bottom of the subsink 133, a swirl stop 141 can be positioned on the bottom surface 140. The swirl stop 141 is simply a narrow rectangular block which has a bottom surface adhered to the bottom surface 140 and a side surface adhered to a lower perimeter wall 138 of the subsink 133 such that it interferes with any swirling action of fluid in the subsink 133 to enhance the draining action of the fluid through a centered drain opening 137.

As in the canisters 4 and 71, the port 121 serves as a receptacle for the injection jet 34 or 106 (not shown), for purposes described above. By introducing the jet 34 or 106 into the port 121, the plunger rod 124 pushes the stopper 132 out of the drain opening 126, thus draining the semi-rigid container 112 and preparing it for flushing and disinfectant.

Referring to FIG. 14, an alternative version of plunger rod 142 is illustrated for use with a modified semi-rigid container 112a. The container 112a is similar in all respects to the container 112, except that it is equipped a continuous bottom 131a with no openings. The plunger rod 142 includes a sharp, trocar-like point 143 on the bottom end thereof, which point 143 is designed to puncture the bottom 131a of the semi-rigid container 112a when engaged by the jet 34 or 106 being introduced into the port 121. Any liquid in the container 112a is thus allowed to drain out through the punctured bottom 131a. The plunger rod 142 can be hollow with openings 144 in the perimeter thereof to facilitate drainage of the container 112a.

Referring to FIG. 15, a second alternative version of plunger rod 151 is illustrated for use with the modified semi-rigid container 112a. Again, the container 112a is similar in all respects to the container 112, except that it is equipped a continuous bottom 131a with no openings. The plunger rod 151 is attached to and extends upward from a bottom surface 152 of a modified subsink 133a, preferably in surrounding relationship with a subsink drain opening 153. The plunger rod 151 also includes a sharp, trocar-like point 154 on the top end thereof, which point 154 is designed to puncture the bottom 131a of the semi-rigid container 112a when it is properly positioned on the upstanding perimeter wall 134 of the subsink 133a, as described above and illustrated in FIG. 13. All liquid waste in the container 112a is thus allowed to drain out through the punctured bottom 131a. Again, the plunger rod 151 can be hollow with openings 155 in the perimeter thereof to facilitate drainage of the subsink 133a.

VII. Operation and Liquid Medical Waste Disposal and Canister Flushing Method

Figure 9:
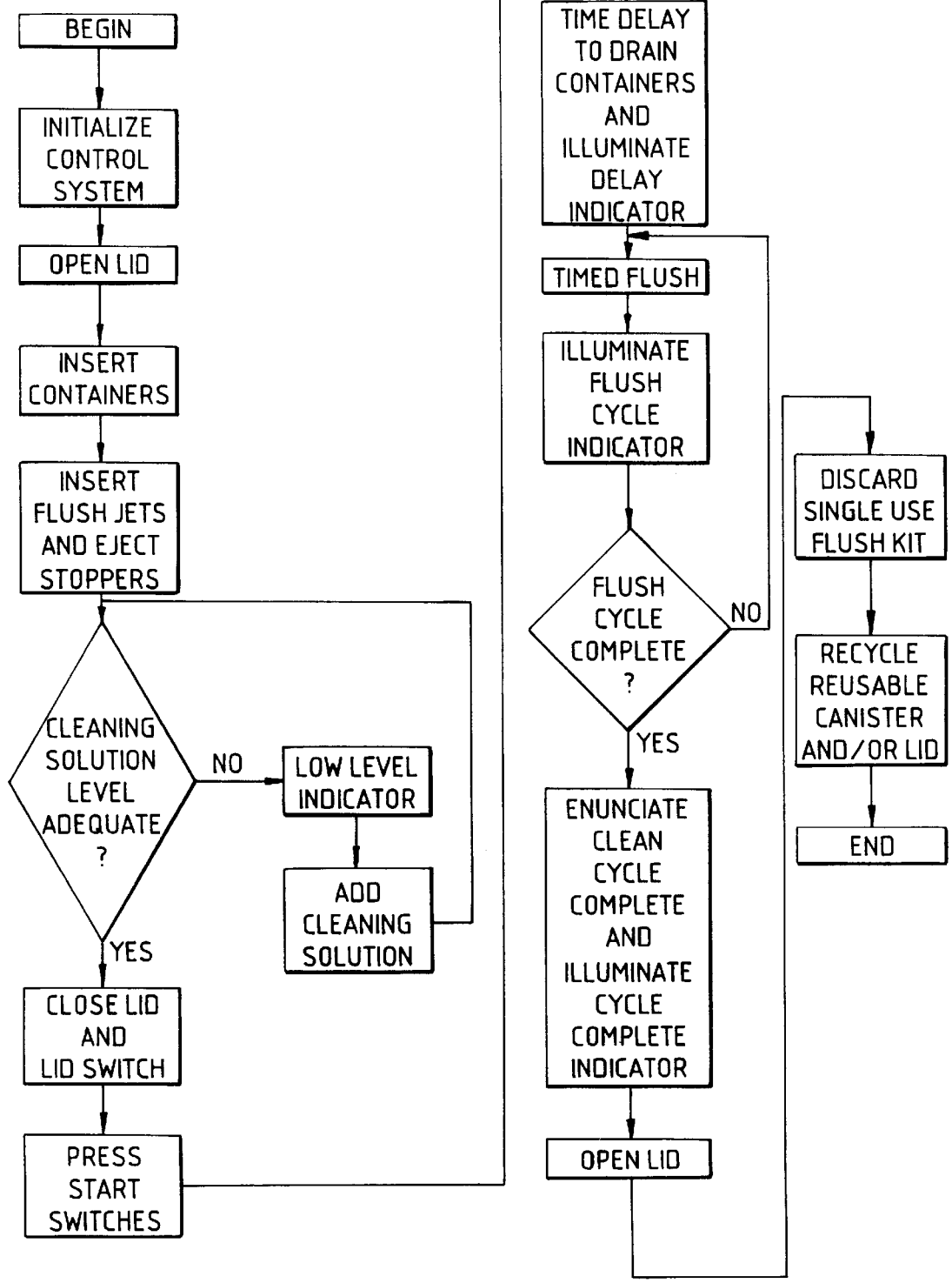
FIG. 9 is a flow chart of a method of liquid waste disposal and canister flushing embodying the present invention.

FIG. 9 comprises a flow chart showing a method of disposing of liquid medical waste and flushing the canisters 4. While the following description is directed to the canister and subsink embodiments illustrated in FIGS. 1–7, the steps are equally applicable to the alternative embodiments illustrated in FIGS. 10–15.

The control system 10 is initialized, for example, by programming the microprocessor 50 with appropriate operating parameters including delay or drain cycle times, flush cycle times, etc. The cabinet lid 14j is opened to access the sink 14k. One or two canisters 4 are placed in respective subsinks 14l, which have circular mouths 14m with diameters intermediate the diameters of the canister lids 4c and bases 4f whereby the canisters 4 extend partway into the subsinks 14l and the canister sidewalls 4g form friction fits with the subsink mouths 14m whereby a friction seal is formed around the circumference of the canister sidewalls 4g.

The injection jets 34 are next connected by removing the caps 12f from the plunger subassemblies 12 to provide access to the canister lid accessory ports 4d wherein the injection jet body lower ends 34c engage the plunger rod upper ends 12e. Pushing the injection jet bodies 34a into the canister lid accessory ports 4d dislodges the plunger stoppers 12d from the canister base drain openings 12a whereby the canisters 4 drain their contents into the subsinks 14l. The cabinet subsink drain openings 14q are sized larger with diameters D1 than the canister base accessory openings 12a with diameters D2 whereby the liquid medical waste from the canisters 4 is substantially instantly drained from the subsinks 14l. In other words, the subsinks 14l have greater flow discharge rate capacities than the canisters 4 whereby backing up of medical waste within the subsinks 14l is avoided.

With the injection jets 34 placed in the canister lid accessory ports 4d, the cabinet lid 14j can be closed, which permits the flush cycles to be commenced or initiated by pressing the start buttons. The cabinet lid 14j can be positioned sufficiently close to the injection jets 34 that the latter are retained in place in the canister lid accessory ports 4d by the cabinet lid 14j during the flush cycle. A timed delay of the commencement of the flush cycle is provided after the cabinet lid 14j is closed and the start buttons are actuated, which delay permits substantially complete drainage of the canisters 4 through the subsinks 14l before the flush cycle commences. Thus, the flush cycle is initiated in substantially empty canisters 4. The microprocessor 50 can be programmable to vary the timed delay for canister draining and for the length of the flush cycle.

As a general guideline, it is desirable to flush the canisters 4 with a volume of solution equal to approximately 3 to 4 times their capacities. The cleaning solution mixture preferably comprises water and a suitable agent for killing virus and bacteria. For example, sodium hypochlorite (i.e., bleach) in a solution of about 1200 to 1400 parts per million with water has generally been found to be suitable. A delay of approximately 8 seconds has been found to be sufficient to drain the canisters 4, and a flush cycle of approximately 45 seconds has generally been found to be sufficient.

The solution mixture is preferably chosen to meet the particular objectives of a disposal and flushing system. For example, disinfection and flushing are generally the primary objectives with liquid medical waste containers 4, which for most reuse purposes do not have to be cleaned to the point where they would be considered sterile, since sterility is normally not required for liquid medical waste canisters. The plunger subassemblies 12 and the canister lids 4c can be disposed of and the container bodies 4a reused at a fraction of the cost of disposing of complete canisters 4 full of liquid medical waste. The lids 4c and the plunger subassemblies 12 would generally be considered "white" trash in medical facilities due to relatively low concentrations of liquid medical waste thereon and thus would not be subjected to the more stringent requirements typically in place for handling and disposing of the actual liquid medical wastes.

The flushed liquid medical waste from the system 2 would mix with the effluent from the medical facility in its plumbing drainage system and could normally be discharged into a municipal sewer system at levels well below the maximums permitted for medical waste effluents.

It is to be understood that while certain forms of the present invention have been illustrated and described herein, it is not to be limited to the specific forms or arrangement of parts described and shown.

What is claimed and desired to be secured by Letters Patent is as follows:

1. A canister usable with a liquid waste disposal and canister flushing system, said flushing system including a flush jet and a cabinet including a subsink, said canister comprising:
   (a) a container with a closed bottom portion which is insertable in said subsink;
   (b) a lid permanently affixed to said container in covering relation with a top portion of said container, said lid including an accessory port sized to accommodate said flush jet; and
   (c) a plunger rod operable to open a drain in said bottom portion of said container to thereby drain said container.

2. A canister as in claim 1, and further comprising:
   (a) a generally cylindrical reusable rigid outer casing including an open top and a closed bottom sized to fit within said subsink;
   (b) a drain opening in said closed bottom of said rigid outer casing; and wherein
   (c) said container is a disposable flexible liner sized to fit within said rigid outer casing with said lid lockably engaging said open top of said rigid outer casing.

3. A canister as in claim 2, and further comprising:
   (a) a drain opening in said closed bottom of said flexible liner;
   (b) a stopper positioned in said liner drain opening; and wherein
   (c) said plunger rod is positioned within said liner and extends upward into said accessory port, said plunger rod being engageable by said flush jet when it is inserted into said accessory port such that said plunger rod is forced downward, said stopper engaging said plunger rod such that said stopper is forced out of said drain opening when said plunger rod is forced downward by said flush jet.

4. A canister as in claim 2, and further comprising:
   (a) a first key shape proximate said open top of said rigid casing; and (b) a second, matching key shape attached to said lid whereby alignment of said first and second key shapes serves to orient said liner to said casing.

5. A canister as in claim 2, wherein:
   (a) said drain opening in said outer casing is filleted to minimize sharp edges.

6. A canister as in claim 1, wherein:
   (a) said container comprises a disposable semi-rigid container which is self supporting; and
   (b) said plunger rod includes a sharp point which penetrates said bottom portion of said semi-rigid container.

7. A canister as in claim 6, wherein:
   (a) said plunger rod is positioned within said container and extends upward into said accessory port, said plunger rod being engageable by said flush jet when it is inserted into said accessory port such that said plunger rod is forced downward to penetrate said container bottom portion.

8. A canister as in claim 6, wherein:
   (a) said plunger rod is affixed to a bottom surface of said subsink and extends upward such that, when said container is positioned in said subsink, said plunger rod punctures said bottom portion of said container.

9. A canister as in claim 1, wherein said container comprises a semi-rigid container which is self supporting, said canister further comprising:
   (a) a drain opening in said bottom portion;
   (b) a stopper extending into said drain opening; and wherein
   (c) said plunger rod is positioned within said container and extends upward into said accessory port, said plunger rod being engageable by said flush jet when it is inserted into said accessory port such that said plunger rod is forced downward, thus forcing said stopper out of said drain opening.

10. A canister as in claim 1, wherein:
    (a) said accessory port has at least one wall which tapers downward and outward to act as a guide for said plunger rod.

11. A flush jet usable with a liquid waste disposal and canister flushing system, said flushing system including a cabinet including a subsink accommodating a canister to be flushed, the canister including an accessory port for accommodating the flush jet, said flush jet comprising:
    (a) a body with upper and lower ends;
    (b) a cleaning solution inlet port at said upper end;
    (c) a water inlet port at said upper end;
    (d) a discharge orifice at said lower end;
    (e) a jet passage extending from said water inlet port to said discharge orifice; and
    (f) a cleaning solution passage extending from said cleaning solution inlet port to said jet passage and forming an intersection therewith at an angle which eliminates any venturi effect on said cleaning solution passage from said jet passage.

12. A flush jet as in claim 11, wherein:
    (a) said lower end of said flush jet body is beveled to securely engage an upper end of a plunger rod positioned in said canister.

13. A control system for a liquid waste disposal and canister flushing system, said flushing system including a flush jet attached to a source of water and a source of cleaning solution, said flush jet being designed for insertion in a canister to be flushed and a cabinet including a subsink for holding the canister during flushing, said system comprising:

(a) a programmed controller programmed to control drain and flush cycles of said system;

(b) a water flow monitor connected to said controller;

(c) a water pressure monitor connected to said controller;

(d) a cleaning solution flow monitor connected to said controller; and (e) flow controllers connected to said source of water and said source of cleaning fluid, and to said controller such that said controller can accurately control the relative concentrations of cleaning fluid to water based upon feedback from said water and cleaning solution flow monitors.

14. A control system as in claim 13, and further comprising:

(a) a display positioned on the cabinet and connected to said controller to display system parameters sensed and/or calculated by said controller.

15. A control system as in claim 13, and further comprising:

(a) a modem connected to said controller to provide remote monitoring of system parameters.

16. A control system as in claim 13, wherein said controller is programmed to store and archive any parameters which are outside of predetermined limits.

17. A liquid waste disposal and canister flushing system, said flushing system including:

(a) a flush jet attached to a source of water and a source of cleaning solution;

(b) a semi-rigid canister to be flushed, said canister including an upper accessory port which accommodates the insertion of said flush jet and a drain opening for draining the contents of said canister;

(c) a cabinet including a sink with a floor; and (d) a subsink which is sized to hold the canister during flushing, said subsink including a basin with a bottom surface which extends below the floor of said cabinet with a subsink drain opening in said basin bottom surface connecting with a sewer system for draining the contents of said subsink, said subsink also including an upwardly extending perimeter wall which extends above the floor of said sink to support said semi-rigid canister.

18. A liquid waste disposal and canister flushing system as in claim 17, wherein said canister further comprises:

(a) a stopper extending into said drain opening; and (b) a plunger rod which is positioned within said canister and extends upward into said accessory port, said plunger rod being engageable by said flush jet when it is inserted into said accessory port such that said plunger rod is forced downward, thus forcing said stopper out of said drain opening.

19. A liquid waste disposal and canister flushing system as in claim 18, wherein said canister accessory port has at least one wall which tapers downward and outward to act as a guide for said plunger rod.

20. A liquid waste disposal and canister flushing system as in claim 17, wherein:

(a) said subsink includes a swirl stopper positioned on said subsink bottom surface.

* * * * *